(12) United States Patent
Keith

(10) Patent No.: US 8,751,434 B2
(45) Date of Patent: Jun. 10, 2014

(54) SIGNAL ANALYSER

(75) Inventor: Robert Keith, Devon (GB)

(73) Assignee: K2 Medical Systems Limited, Tamar Science Park, Derriford, Plymouth, Devon (GB)

( * ) Notice: Subject to any disclaimer, the term of this patent is extended or adjusted under 35 U.S.C. 154(b) by 68 days.

(21) Appl. No.: 12/935,019

(22) PCT Filed: Mar. 30, 2009

(86) PCT No.: PCT/GB2009/000847
§ 371 (c)(1),
(2), (4) Date: Nov. 24, 2010

(87) PCT Pub. No.: WO2009/122161
PCT Pub. Date: Oct. 8, 2009

(65) Prior Publication Data
US 2011/0161277 A1     Jun. 30, 2011

(30) Foreign Application Priority Data
Mar. 29, 2008   (GB) .................................... 0805725.9

(51) Int. Cl.
G06F 9/44       (2006.01)
G06N 7/02       (2006.01)
G06N 7/06       (2006.01)

(52) U.S. Cl.
USPC ......................................................... 706/52

(58) Field of Classification Search
None
See application file for complete search history.

(56) References Cited

U.S. PATENT DOCUMENTS

| 5,123,420 A | 6/1992 | Paret |
| 5,311,874 A | 5/1994 | Baumann et al. |
| 5,442,940 A | 8/1995 | Secker et al. |
| 5,609,156 A * | 3/1997 | Keith et al. .................. 600/483 |
| 2002/0068874 A1* | 6/2002 | Zuckerwar et al. ........... 600/511 |

(Continued)

FOREIGN PATENT DOCUMENTS

| EP | 0808603 A2 | 11/1997 |
| WO | 9325971 A1 | 12/1993 |
| WO | W09325971 A1 | 12/1993 |
| WO | 2008094125 A1 | 8/2008 |

OTHER PUBLICATIONS

'Foetos: An expert system for fetal assessment': Alonso, 1991, IEEE, 0018-9294/91, pp. 199-211.*

(Continued)

*Primary Examiner* — Kakali Chaki
*Assistant Examiner* — Peter Coughlan
(74) *Attorney, Agent, or Firm* — Barlow, Josephs & Holmes, Ltd.

(57) ABSTRACT

A signal analyzer is operable to receive one or more signals and then to analyze the signals with respect to particular properties before outputting an indication as to the classification of the signal with respect to each property. The indication is in the form of a plurality of belief index ratings, the magnitude of each belief index rating relating to the likelihood of the corresponding classification being accurate. This is achieved by incrementing or decrementing one or more individual belief index values in response to the identification of predetermined signal features by the signal processing means. Which belief index values are incremented or decremented and by how much is determined by the particular signal feature detected. Data is retrieved from a suitable look up table. Data storage is operable to store a copy of the received signals for future reference.

18 Claims, 4 Drawing Sheets

(56) References Cited

U.S. PATENT DOCUMENTS

| | | | |
|---|---|---|---|
| 2005/0267376 A1 | 12/2005 | Marossero et al. | |
| 2005/0267377 A1* | 12/2005 | Marossero et al. | 600/511 |
| 2006/0149597 A1* | 7/2006 | Powell et al. | 705/2 |
| 2007/0276251 A1* | 11/2007 | Orenstein et al. | 600/459 |
| 2007/0282633 A1* | 12/2007 | Haider et al. | 705/3 |
| 2009/0281441 A1* | 11/2009 | Zhang et al. | 600/516 |

OTHER PUBLICATIONS

'A tutorial on learning with Bayesian Neworks': Heckerman, 1996, Microsoft Technical report MSR-TR-95-06.*

'Choice of error cost function for training unobservable nodes in Bayesian networks': Kwoh, 1997, IEEE, 0-7803-3755, pp. 565-574.*

Amin, S., Byington P.E., Carl, Watson, M, "Fuzzy Inference and Fusion for Health State Diagnosis of Hydraulic Pumps and Motors", North American Fuzzy Information Processing Society (NAFIPS) 2005, Annual Meeting in Detroit, MI USA, Jun. 26-28, 2005, Piscataway, NJ, USA, IEEE, Jun. 26, 2006, pp. 13-18, XP010887959, ISBN: 978-0-7803-9187-1, p. 16, section "v. Fusion of dynamic and performance results" abstract—Figure 1.

Cao, J., and Sanders, D. B., "Multivariate discriminant analysis of the electromyographic interference pattern: statistical approach to discrimination among controls, myopathies and neuropathies", Medical and Biological Engineering and Computer, Springer, Heildelberg, DE, vol. 34, No. 5, Sep. 1, 1996, pp. 369-374, XP000626986, ISSN: 0140-0188, p. 373, section 6.2 "Likelihood index Table 5".

* cited by examiner

SIGNAL ANALYSER

The present invention relates to a signal analyser and in particular to a signal analyser operable to provide an indication of the classification of the signal corresponding to one of a plurality of potential signal classifications.

In many situations electronic sensing instruments are used to monitor various parameters. The signals generated by the sensing instruments may be displayed for review by appropriate personnel. Additionally, such signals may be automatically monitored and analysed by a signal analyser. The signal analyser may be operable to output an alarm should the signal cross a particular threshold or exhibit particular predetermined features.

Known signal analysers are prone to positive and negative false alarms; that is, raising an alarm unnecessarily and not raising an alarm when necessary, respectively. In some systems, the false alarm rate can be sufficiently high that in practice, the alarm is frequently ignored or even disabled. On the other hand, whilst review and analysis of the displayed signal by a human can sometimes lead to a more accurate or sympathetic interpretation of potential problems evidenced by the signal, correct interpretation still requires specialised training, considerable experience, skill and alertness. Even with all these qualities, it may be possible for a human operator to miss more subtle patterns or events buried in the overall signal that may indicate a possible underlying trend.

A particular range of examples of such a situation would be provided by modern medicine. In many cases a patient in a hospital is connected to one or more instruments operable to sense and display information related to selected physiological parameters.

It is therefore an object of the present invention to provide a signal analyser that at least partially overcomes or alleviates the above problems.

According to a first aspect of the present invention there is provided a signal analyser comprising: signal receiving means operable to receive a signal for analysis; signal processing means operable to process the received signal and identify the occurrence of any of a plurality of predetermined signal features; a classification engine operable to increment or decrement one or more individual belief index values in response to the identification of predetermined signal features, each individual belief index corresponding to one of a plurality of potential signal classifications; and means for providing an indication of the classification of the signal based on the individual belief index values.

Such a signal analyser is operable to provide information as to the relative likelihood of a signal being classified into a particular category. A relatively inexperienced operator can thus rapidly appreciate the overall classification of the signal and whether any closer monitoring or intervention may be required.

Belief index values may be incremented or decremented according to any suitable criteria or algorithm. In some embodiments, belief index values may be incremented or decremented according to a suitable look up table of increments and/or decrements corresponding to the feature or features identified in the signal. The increments or decrements may be varied according to absolute or relative properties of the detected feature or features. The increments or decrements may be filtered by a temporal window. Such a temporal window may provide a higher weighting to more recent features. Increment or decrement in response to a particular feature may be applied to only one or to more than one belief index value. In such cases, the increment or decrement need not be the same for each belief index value.

Belief index values may be used to calculate belief index ratings. By considering the relative belief index rating of each potential signal classification an indication as to the overall signal classification can be obtained. Preferably, the belief index ratings are each limited to a particular range. As an example the range may be between 0 and 1. In such a scheme, higher ratings may indicate a greater prospect that the particular classification of the signal is accurate. Of course, it is evident to the skilled man that an opposite ratings scheme could apply, if desired.

The belief index values may be restricted to a particular range. The belief index ratings may be calculated from the belief index values by use of a suitable function. Preferably, the function is not a linear function of belief index value. Most preferably, the function rises relatively slowly at either end of the range of belief index values and relatively rapidly in the middle of the range of belief index values. One such suitable function has the form $y=1/(1+e^{-x})$ wherein y is the belief index rating and x is the belief index value.

The belief index ratings may provide a classification of the signal. In a first instance, the belief index ratings may be provided to an operator in order that the operator may make a judgement as to the classification of the signal. In another instance, the analyser may automatically classify the signal, if a particular belief index rating exceeds a predetermined classification threshold level. In the event that two or more belief index ratings exceed the predetermined classification threshold level the signal can be assigned the classification of the highest belief rating or be assigned a joint classification. Once a signal has been classified, it will retain the classification so long as the relevant belief index rating does not drop below a predetermined de-classification threshold level and so long as no other belief index rating exceeds the predetermined classification threshold level. Preferably, the de-classification threshold level is lower than the classification threshold level. This allows for an element of hysterisis in assigning a classification.

Preferably, the signal analysed is an ongoing signal. The analyser may be operable to periodically sample the signal and update each belief index value and hence update each belief index rating. The analyser may be operable to analyse only a particular selected portion of the signal. Typically, the analyser may be operable to increment or decrement each belief index at regular time intervals on the basis of features identified in the signal during a pre-selected number of previous time intervals. As an illustrative example, the belief indexes could be recalculated every, say, minute on the basis of signal features detected in the previous, say, 15 minutes.

The analyser may be operable to classify the signal with respect to a plurality of signal properties. Each signal property may have two or more possible classifications, each classification having a corresponding belief index. Classification with respect to different properties may rely on detecting different signal features for each property.

The indication as to the classification of a signal may be displayed on a suitable display unit. The indication may be displayed numerically, textually or graphically or even by a combination of any two or all three forms. In the event that the indication is displayed graphically, it preferably takes the form of a histogram, with each bar corresponding to a particular classification and the area of bar corresponding to the belief index rating of the classification. This provides a readily interpretable representation of the likely classification of the signal.

If the signal is classified with respect to two or more properties, the indications as to classification with respect to each property may be displayed. Each classification indication may be displayed using the same format or different formats. The displayed classification indications may be displayed adjacent to each other on the display unit. Alternatively, only one or more selected classification indications may be displayed, when desired.

The analyser may be operable to generate an alarm or notification in response to the determination of a particular classification. Additionally or alternatively, the analyser may be operable to generate an alarm or notification in response to the detection of particular predetermined signal features or predetermined signal feature thresholds. Typically, a notification may be generated in response to a first signal feature or signal feature threshold and an alarm may be generated in response to a second signal feature or signal feature threshold. Typically, the second signal feature or signal feature threshold would be indicative of a more extreme or potentially dangerous classification. In some embodiments, there may be a number of different alarms generated in response to further signal features or signal feature thresholds. The different alarms may indicate different levels of potential danger.

The generated alarm or notification can be visual, audible or both. Additionally or alternatively, the generated alarm or notification can be transmitted to a remote location. The transmission can take place over any suitable means including via one or more wired, wireless or combined links or networks. This allows a supervisor or more experienced operator at a remote location to be warned of a possible problem based on the evidence of the signal. In addition to the transmission of an alarm or notification, signal data may also be transmitted. This can allow the supervisor or more experienced operator to review the signal to determine what, if any, action is necessary.

The signal processing means may be operable to detect any suitable features within the signal For example the detected features may include, but are not limited to, any one of: current signal level, signal peak detection, peak height, peak area, peak width, average signal level, signal level variation, signal frequency, signal quality or similar. With respect to any or all of the above features, the detected feature may be subject to further identification discriminated by threshold, overall value or similar.

The analyser may be operable to analyse two or more signals substantially simultaneously. The two or more signals may be related signals. In such cases, increment and decrement of one or more of the belief indexes for one or more classifications in respect to one or more properties may be based on features detected in any of the signals.

The signal analyser may incorporate an operator input interface. The interface may allow the operator to select a particular period of the signal for analysis, select a particular property of the signal for classification, vary the parameters for identifying a particular feature, vary the time intervals for recalculation or similar.

The analyser may incorporate suitable data storage means. This allows received signals to be stored for future review and reanalysis.

Any suitable sensing device may be used to generate the signal for analysis. In particular, the sensing device may be a medical sensing device.

The medical sensing device may be a device operable to sense the uterine contractions of a pregnant woman and foetal heart rate. The contractions may be monitored using a strain gauge or by suitably located pressure sensor. The foetal heart rate can be monitored using ultrasound or by an electrocardiogram (ECG). Such a device, which usually produces a continuous time-varying, parallel trace indicating uterine contractions and foetal heart rate called a cardiotocogram (CTG), is commonly called a CTG monitor. These signals may be analysed with respect to any one or more of the following properties baseline heart rate, heart rate variability, heart rate acceleration (i.e. a period of increased heart rate), heart rate deceleration (i.e. a period of decreased heart rate), uterine contraction frequency, uterine pushing classification, sinusoid classification, bimodal classification and sensing device output signal quality. A heart rate acceleration for example, may be classified as present or absent, or a heart rate deceleration may be further classified by its size and its timing in relation to uterine contractions.

According to a second aspect of the present invention there is provided a method of signal analysis comprising: processing a signal to identify the occurrence of any of a plurality of predetermined signal features; incrementing or decrementing one or more individual belief index values in response to the identification of predetermined signal features, each individual belief index corresponding to one of a plurality of potential signal classifications; and providing an indication of the classification of the signal based on the individual belief index values.

The method of the second aspect of the present invention may incorporate any or all features of the first aspect of the present invention as desired or as appropriate.

In order that the invention is more clearly understood, one embodiment will be described in greater detail below by way of example only and with reference to the accompanying drawings, in which.

The present invention provides a signal analyser 100 that is operable to receive one or more signals and then to analyse said signals with respect to particular properties before outputting an indication as to the classification of the signal with respect to each property. Typically this indication is in the form of a plurality of belief index ratings, the magnitude of each belief index rating relating to the likelihood of the corresponding classification being accurate.

Figure 1:
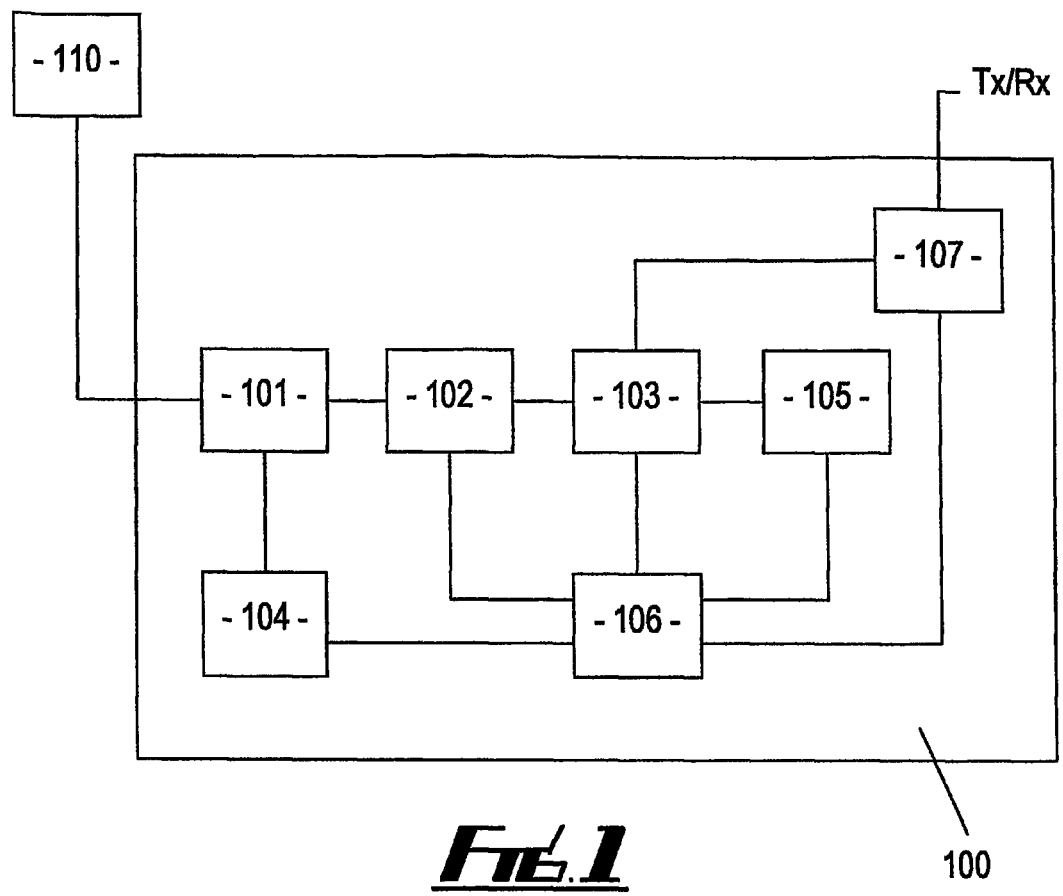
FIG. 1 is a schematic block diagram of a signal analyser according to the present invention.

Turning now to FIG. 1, the signal analyser 100 comprises signal receiving means 101, signal processing means 102, a classification engine 103, a data storage means 104, a display means 105, an operator interface 106 and a notification/alarm unit 107.

The signal receiving means 101 is operable to receive one or more input signals for analysis from one or more external sensing instruments 110. The signal processing means 102 is operable to process the received signals and identify the occurrence of any of a plurality of predetermined signal features within the received signals.

The classification engine 103 is operable to maintain two or more belief indexes corresponding to two or more possible classifications of a received signal in respect of a particular signal property. This is achieved by incrementing or decrementing one or more individual belief index values in response to the identification of predetermined signal features by the signal processing means 102.

Which belief index values are incremented or decremented and by how much is determined by the particular signal feature detected. Typically, this data is retrieved from a suitable look up table stored in the data storage means 104. The data storage means 104 is also operable to store a copy of the received signals for future reference.

In a usual mode of operation, the analyser 100 is operable to analyse the signal during a temporal window ending at the present time. Periodically, the start of the temporal window is redefined and the belief index values are recalculated. The interval between recalculations is typically an integral fraction of the duration of the temporal window. Upon recalculation, each belief index value is incremented or decremented according to the features detected during the temporal window. The increment or decrement for features occurring early in the temporal window may be scaled appropriately. At the initiation of analysis of a signal each belief index has an equal belief index value. Each belief index value is also range limited. In a suitable example, the values may range between −6 and 6.

Figure 2:
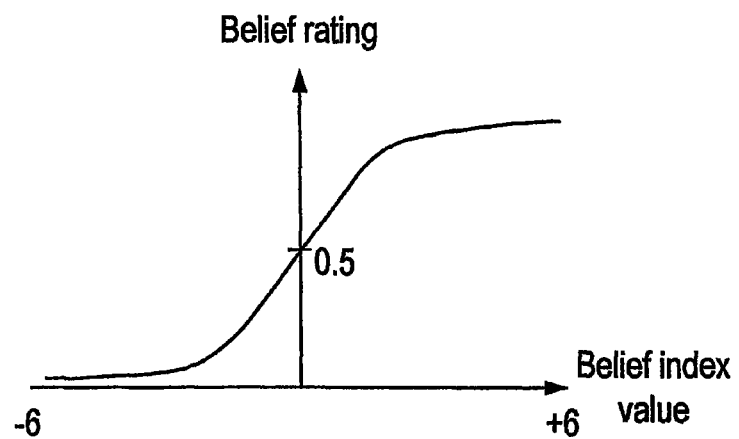
FIG. 2 shows a function suitable for calculating belief.

The belief index values are then used to calculate a belief index rating for each possible classification by means of a suitable function such as $y=1/(1+e^{-x})$ wherein y is the belief index rating and x is the belief index value. Such a function is illustrated in FIG. 2. The belief index rating is thus a figure between 0 and 1, a larger figure indicating greater confidence that a particular classification is accurate.

The belief index ratings each start the initial signal classification process with the value 0.5. The belief index ratings are updated by the classification engine in response to signal features within successive time window. A firm classification of the signal according to a particular signal property can then be made once one belief index rating for that property reaches a threshold, say, 0.75. The classification is then held whilst this particular belief index rating maintains above a second threshold, say 0.5, and whilst no other belief index rating rises above the first threshold (0.75). This adds a stabilising element of hysteresis into the classification.

The display means 105 is operable to display the indication of the classification of the signal based on the individual belief index values. The display means 105 may also be operable to display a direct representation of the input signal.

Typically, the belief index ratings for each classification are displayed as a histogram, each bar corresponding to a classification and the area of each bar corresponding to the belief rating. This allows an operator to readily appreciate the likely classification of the signal. Specific examples of such histograms will be explained in more detail below.

Specific signal features or classifications may be identified on the representation of the input signal by suitable notifications or alarms. These may include coloured highlighting on or over the representation. Specific examples of such highlighting will be explained in more detail below.

The input interface 106 allows an operator to control the operation of the analyser 100. This control may vary the operation of any of the signal processing means 102, classification engine 103, data storage means 104 or display 105.

The notification/alarm unit 107 is operable to generate an alarm or notification in response to the determination of particular classifications or reclassifications by the classification engine and is additionally or alternatively operable to generate an alarm or notification in response to the detection and identification of particular predetermined signal features or predetermined signal feature thresholds by the signal processing means 103. Typically, notifications are generated in response to classifications or reclassifications of the signal with respect to particular properties that are not considered to be of particular seriousness and/or to the detection of particular signal features or the exceeding of particular signal thresholds that are similarly not considered to be of particular seriousness. In the event that there are a variety of predetermined levels of seriousness associated with any above classification, reclassification, feature or threshold levels of notifications can be issued. Typically, notifications may be purely visual and may take the form of highlighting part of the displayed signal or adding a text note or icon to the displayed signal. If an icon is displayed this may be selectable by the user to display textual information relating to the notification.

In response to more serious classifications/reclassifications, detected/identified signal features or signal thresholds exceeded an alarm is generated. As above there may be several levels of alarm possible depending on the perceived seriousness of the classification, reclassification, feature or threshold levels. Typically, the generated alarm is both visual and audible. The visual and audible indications of the alarm are typically more extreme for more severe alarm levels.

The notification/alarm unit 107 is additionally operable to transmit data from the analyser to external equipment or locations and to receive data from external equipment or locations. Typically, the notification/alarm unit 107 can activate an alarm in response to a belief index rating exceeding a particular value for a particular classification. Additionally, the notification/alarm unit 107 may be operable to transmit notifications, alarms, raw signal data and or belief index data to external equipment or locations for review either in response to an alarm or to input from the interface 106. This allows an inexperienced operator to rapidly obtain the opinion on the signal of a more experienced operator, who may then decide upon what action, if any, is required in response.

It is also possible to archive any analysed signal either in the data storage means 104 and/or by transferring stored data to external storage means. The transfer can be undertaken in real time or after the conclusion of signal analysis. The data archived should include any notifications or alarms generated so that an audit of operator performance may be undertaken after the event.

In order that the operation of the analyser 100 is more clearly understood, a particular example of an analyser operation is described below. The particular operation described relates to the analysis and classification of signals received from a device operable to sense the uterine contractions of a pregnant woman and a foetal heart rate. The contractions may be monitored using a strain gauge or by monitoring intrauterine pressure. The foetal heart rate can be monitored using ultrasound or, more invasively, by an electro-cardiogram (ECG). The resultant received signals provide a continuous time-varying, pair of parallel traces indicating uterine contractions and foetal heart rate commonly described as a cardiotocogram (CTG) or a CTG monitor. It is of course possible to utilise the invention to monitor other types of signals if required or desired.

Figure 3:
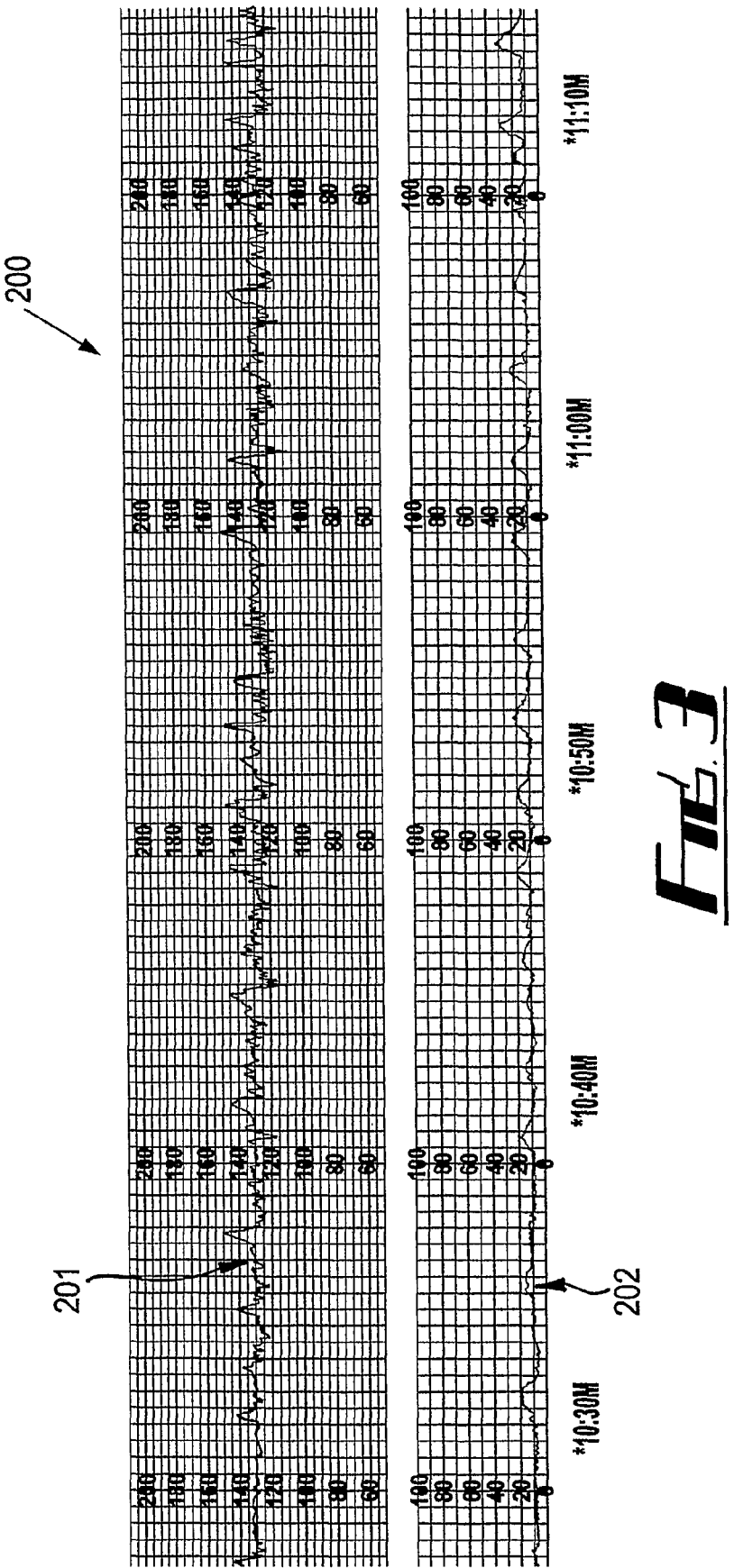
FIG. 3 is a schematic illustration of a typical cardiotocogram.

Turning now to FIG. 3, an example of a raw cardiotocogram 200 is shown. In the prior art, such a cardiotocogram 200 may be presented directly to medical personnel on a suitable display unit. Such personnel may monitor the displayed cardiotocogram 200 for evidence of any potential dangers. Typically, many of the features of the cardiotocogram will be assessed by eye, with a simple alarms being automatically generated only in particularly clearcut instances. In this cardiotocogram 200, the upper trace 201 indicates the foetal heart rate over time and the lower trace 202 indicates uterine contractions over time.

Figure 5:
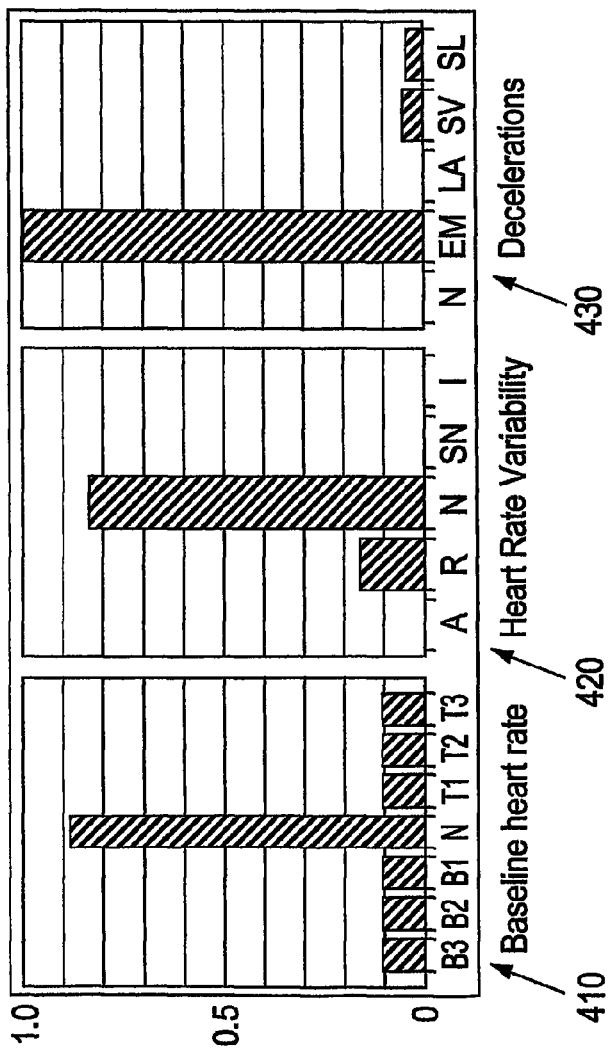
FIG. 5 is a schematic illustration of belief histograms according to the present invention.

As described above, identified features of the cardiotocogram 300 are classified by use of belief index ratings. The belief index ratings are typically also displayed using said display means in the form of one or more histograms. Three such Histograms 410, 420, 430 are shown in FIG. 5, by way of example. The histograms 410, 420, 430 provide a visual indication of the likelihood that features of the cardiotocogram 300 are indicative of a particular classification.

In the example shown, there are the first histogram 410 is indicative of the classification of the foetal heart rate signal 301 with regard to baseline heart rate. In this example, a plurality of possible classifications B3 (severe bradycardia), B2 (bradycardia), B3 (mild bradycardia), N (normal), T1 (mild tachycardia), T2 (tachycardia) and T3 (severe tachycardia) are each represented by a separate belief index within the histogram 410. It is also clear that in this case, the belief index rating for classification normal is high whilst all the other belief index ratings are low. This is therefore indicative that the signal with respect to the property foetal baseline heart rate should be classified as normal.

In the present example, classification is achieved by sampling the signal periodically (say once per minute) throughout the temporal window by means of the signal processing means 102. For each sample, it is determined by the classification engine 103 whether the sampled value lies within a range corresponding to one of the possible classifications. The classification engine 103 will then increment the corresponding belief index value and then decrement all the other belief index values. The magnitude of the increment or decrement will be determined by a stored look up table of increments and decrements corresponding to the particular sample value.

Figure 6:
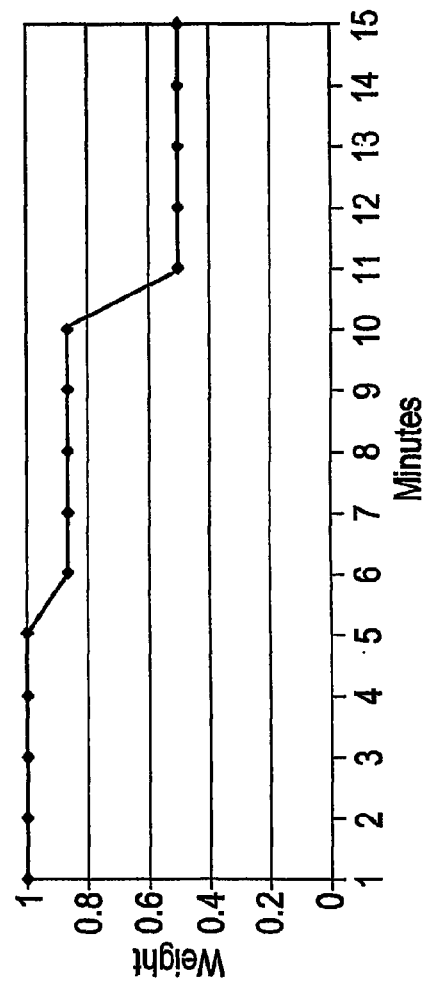
FIG. 6 is a schematic illustration of a temporal window that may be applied to signals processed according to the present invention.

The temporal window may be a window such as that illustrated in FIG. 6. In such a window, each sampled value is assigned a weighting factor. In such cases, the increment or decrement is then multiplied by the weighting factor before being applied to the relevant belief index value by the classification engine 103. This enables more recent samples to take a greater weight in the determination of signal classification.

Turning now to the histogram 420, this classifies the foetal heart rate signal with regard to heart rate variability. In this example, a plurality of possible classifications of the variability A (absent), R (reduced), N (normal), SN (super normal) and I (increased) are each represented by a separate belief index within the histogram 420. It is also clear that in this case, the belief index rating for classification normal is high, the belief index rating for classification reduced is low and all the other belief index ratings are substantially zero. This is therefore indicative that the signal should be classified as normal with respect to the property foetal baseline heart rate variability.

In the present example, classification is achieved by sampling the signal variation over successive periods within a temporal window (say fifteen one minute periods) by means of the signal processing means 102. For each sample, it is determined by the classification engine 103 whether the variation in the sampling window lies within a range corresponding to one of the possible classifications. The classification engine 103 will then increment the corresponding belief index value and then decrement all the other belief index values. In the event that the sampled variation corresponds to none of the possible classifications, all belief index values are decayed. The magnitude of the increment or decrement will be determined by a stored look up table of increments and decrements corresponding to the particular sample value. Similarly to the baseline heart rate example, the temporal window may be weighted towards more recent results.

It is also possible to perform a classification on short term variation of heart rate. This would involve identifying any short term variation (STV) features within each of the sample periods within the temporal window using the signal processing means. In the event that such STV features are identified, the belief engine 103 will classify the STV features as either low or normal and increment a corresponding belief index value accordingly, whilst decrementing the other belief index value. In the event that no STV features are identified both belief index values will be decremented. As above, the magnitude of the increment or decrement will be determined by a stored look up table of increments and decrements corresponding to the particular identified STV feature and the temporal window may be weighted towards more recent results.

Turning now to the histogram 430, this classifies the foetal heart rate signal with regard to heart rate decelerations. In this example, a plurality of possible classifications of the detected foetal heart rate decelerations N (none), EM (early/mild), LA (late), SV (severe) and SL (shallow late) are each represented by a separate belief index within the histogram 430. It is also clear that in this case, the belief index rating for classification early/mild is high, the belief index rating for classifications severe and shallow late are low and all the other belief index ratings are substantially zero. This is therefore indicative that the signal should be classified as early/mild with respect to the property foetal heart rate decelerations.

In the present example, classification is achieved by detecting and identifying the occurrence of foetal heart rate deceleration events within a temporal window (say fifteen minutes) by means of the signal processing means 102 and further detecting and identifying related uterine activity, for example contractions, taking place at or around the same time. The detection and identification of deceleration and/or contraction features can be achieved by use of any suitable algorithm. For each identified deceleration event and associated uterine activity, the signal processing means 102 determines whether the deceleration event lags or leads the related uterine activity and by how much and further determines the magnitude of the deceleration event in relation to the uterine activity. These determinations may be made by any suitable technique such as centroiding. For each event, it is determined by the classification engine 103 whether the lag/lead is classified as none, early or late and whether the magnitude is classified as shallow, moderate or severe. The classification engine 103 will then increment, decrement or leave steady each of the belief index values. The magnitude of the increment or decrement will be determined by a stored look up table of increments and decrements corresponding to the particular sample value.

It is also possible to classify the signal with respect to foetal heart rate acceleration events. In such a scenario the signal could be classified according to belief indexes for no accelerations present or accelerations present. Acceleration events could be detected and identified by the signal processing means which would be further operable to determine the magnitude of such events. The classification engine would then classify the events as none, insignificant, shallow, moderate or severe. The none present belief index value would then be incremented if no accelerations were detected, the accelerations belief index value being correspondingly decremented; in the case where accelerations were detected, the accelerations present belief index value would then be incremented and the none present belief index value would be correspondingly decremented.

In a similar manner to the above, it is possible to classify the cardiotocogram in respect of other signal properties such as uterine contraction frequency, uterine pushing classification, sinusoid classification, bimodal classification and sensing device output signal quality.

Once signal features are identified and belief index ratings are calculated it is possible to classify the signal according to the various signal properties. As will be apparent from the above, it is possible to periodically reclassify the signal, thus iteratively developing the belief index ratings. In this way the evolution of the signal from one classification to another can be clearly observed.

When a signal is classified (or reclassified) with respect to a particular property, or when particular features are identified in the signal, these may generate a notification and/or an alarm. Typically there is a range of notifications or alarms that may be generated depending on the nature of the classification/feature an its potential seriousness. These notifications and alarms can be output visually and if required also audibly to a operator. In particular visual notifications and/or alarms may be displayed alongside the belief histograms and/or over a representation of the signal.

Figure 4:
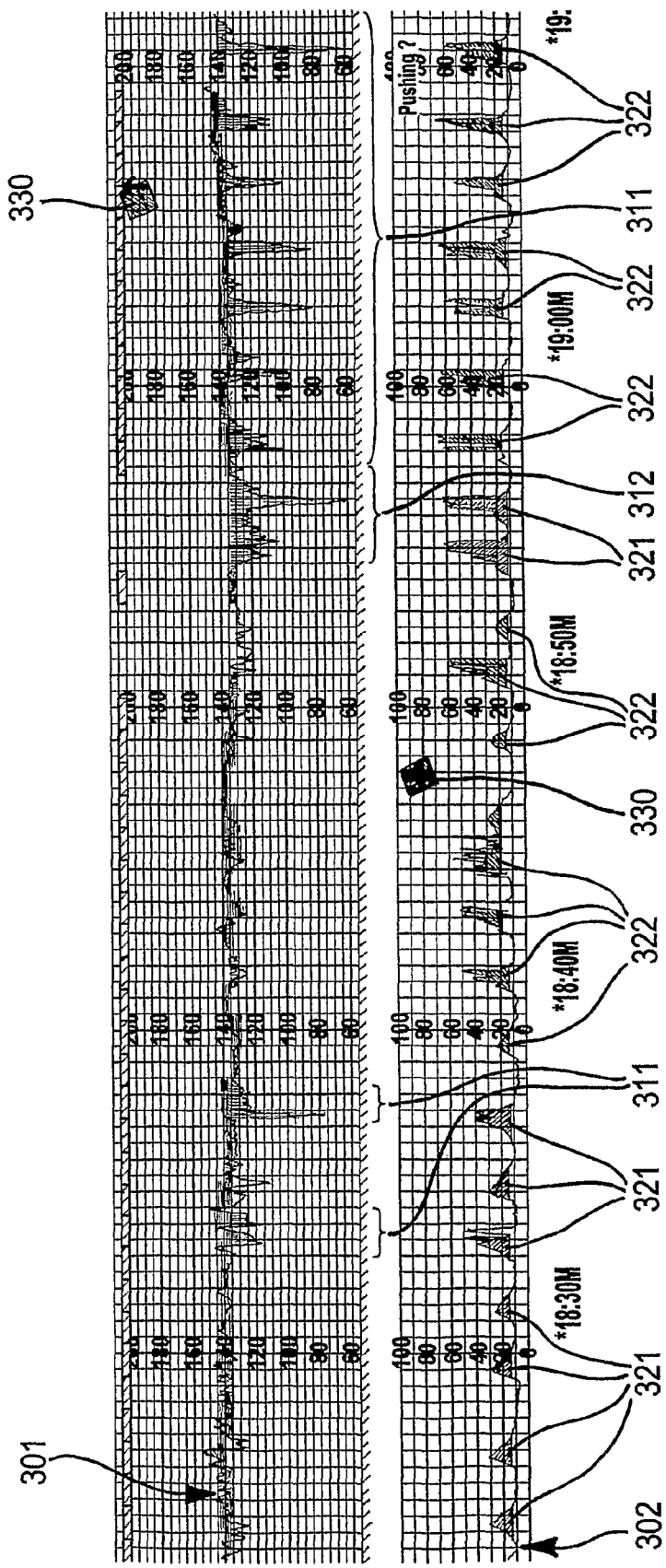
FIG. 4 is a schematic illustration of a typical cardiotocogram including notifications according to the present invention.

Turning now to FIG. 4, an example of how notifications and/or alarms can be displayed over a cardiotocogram 300 on the display means 105 of the signal analyser 100 is shown. As in the generic example of a cardiotocogram the upper trace 301 records foetal heart rate and the lower trace 302 records uterine contractions. In the cardiotocogram 300, various features 311, 312, 313, 314, 321, 322 of each trace 301, 302 are notified to an operator by highlighting upon the display. The highlighting is colour coded to indicate the identification, importance and/or potential danger of such features.

For instance, turning to the foetal heart rate trace 301, there are a number of deceleration events 311 highlighted in a first manner. The magnitude of one of the deceleration events 312 is classified as more severe than the other events 311 and it is thus highlighted differently. Similarly, other less prominent features of the trace 301 are highlighted 313, 314, such that the attention of medical personnel is drawn to these features.

Turning now to the uterine contraction trace 302, a plurality of contraction features 321, 322 are highlighted, the particular nature of the highlighting 321, 322 indicating the classification of the contraction features 321, 322. Additionally displayed are operator selectable notifications 330 generated in response to the evolution of the classification of the signal with respect to one or more particular properties or to the identification of particular signal features. When selected, such notifications may display additional information, which may be textual information, to an operator relating to the particular nature of the change of classification or the particular nature of the identified feature.

It is of course to be understood that the invention is not to be restricted to the details of the above embodiment, which is described by way of example only.

The invention claimed is:

1. A signal analyser for analysing and classifying an ongoing signal, the signal analyser comprising:
a signal receiving device operable to receive a signal for analysis;
a signal processing device in communication with said signal receiving device;
a software application running on said signal processing device operable to
process the received signal and
identify the occurrence of any of a plurality of predetermined signal features,
one or more belief index values, each distinct belief index value corresponding to one of a plurality of potential signal classifications,
said software application including a classification engine operable to automatically increment or decrement said one or more distinct belief index values in response to the identification of predetermined signal features,
after said belief index values are increased or decreased in response to identification of predetermined signal features, said belief index values being used to calculate belief index ratings, wherein each belief index rating has a magnitude, said magnitude relating to the likelihood of the corresponding classification being accurate, and by considering the relative belief index rating of each potential signal classification an indication as to the overall signal classification is obtained; and
a notification unit in communication with said signal processing device, said notification unit being responsive to said classification engine for providing an indication of the classification of the signal based on the individual belief index;
wherein said software application is operable to increment or decrement said belief index values according to an algorithm or a look up table of increments and/or decrements corresponding to the feature or features identified in the signal.

2. A signal analyser as claimed in claim 1 wherein the increments or decrements are varied according to absolute or relative properties of the detected feature or features or wherein increments or decrements in response to a particular feature are applied to only one or to more than one belief index value and the increment or decrement need not be the same for each belief index value.

3. A signal analyser as claimed in claim 1 wherein the increments or decrements are filtered by a temporal window.

4. A signal analyser as claimed in claim 1 wherein the belief index ratings are calculated from the belief index values by use of a suitable function which rises relatively slowly at either end of the range of belief index values and relatively rapidly in the middle of the range of belief index values.

5. A signal analyser as claimed in claim 1 wherein the belief index ratings are provided to an operator in order that the operator may make a judgment as to the classification of the signal or wherein the analyser automatically classifies the signal, either if a particular belief index rating exceeds a predetermined classification threshold level or if two or more belief index ratings exceed the predetermined classification threshold level wherein the signal is assigned the classification of the highest belief rating or a joint classification.

6. A signal analyser as claimed in claim 5 wherein once a signal has been classified, it will retain the classification so long as the relevant belief index rating does not drop below a predetermined de-classification threshold level and so long as no other belief index rating exceeds the predetermined classification threshold level, the de-classification threshold level being lower than the classification threshold level.

7. A signal analyser as claimed in claim 5 wherein said software application is operable to classify the signal with respect to a plurality of signal properties and each signal property may have two or more possible classifications, each classification having a corresponding belief index, classification with respect to different properties relying on detecting different signal features for each property.

8. A signal analyser as claimed in claim 5 wherein said notification unit comprises a display unit and wherein the indication as to the classification of a signal is displayed on said display unit and further wherein the indication is displayed numerically, textually or graphically wherein in the event that the indication is displayed graphically, it takes the form of a histogram, with each bar corresponding to a particular classification and the area of bar corresponding to the belief index rating of the classification and wherein if the signal is classified with respect to two or more properties, the indications as to classification with respect to each property are displayed.

9. A signal analyser as claimed in claim 5 wherein said software application is operable to generate an alarm or notification in response to the determination of a particular classification or in response to the detection of particular predetermined signal features or predetermined signal feature thresholds.

10. A signal analyser as claimed in claim 9 wherein a notification is generated in response to a first signal feature or signal feature threshold and an alarm is generated in response to a second signal feature or signal feature threshold, the second signal feature or signal feature threshold being indicative of a more extreme or potentially dangerous classification.

11. A signal analyser as claimed in claim 9 further comprising a transmitter device wherein the generated alarm or notification is transmitted to a remote location and in addition to the transmission of an alarm or notification, signal data may also be transmitted.

12. A signal analyser as claimed in claim 1 wherein said software application is operable to periodically sample the signal and update each belief index value and hence update each belief index rating and wherein said software application is operable to increment or decrement each belief index at regular time intervals on the basis of features identified in the signal during a pre-selected number of previous time intervals.

13. A signal analyser as claimed in claim 1 wherein said software application is operable to detect any one of: current signal level, signal peak detection, peak height, peak area, peak width, average signal level, signal level variation, signal frequency, signal quality or similar and wherein the detected features are subject to further identification discriminated by threshold, overall value or similar.

14. A signal analyser as claimed in claim 1 wherein said software application is operable to analyse two or more signals substantially simultaneously wherein increment and decrement of one or more of the belief indexes for one or more classifications in respect to one or more properties are based on features detected in any of the signals.

15. A signal analyser as claimed in claim 1 further comprising an operator input interface in communication with said signal processing device, said software application being operable for receiving input from said interface to select a particular period of the signal for analysis, select a particular property of the signal for classification, vary the parameters for identifying a particular feature, or vary the time intervals for recalculation.

16. A signal analyser as claimed in claim 1 further comprising a data storage device.

17. A signal analyser as claimed in claim 1 further comprising a sensing device in communication with said signal receiving device, said sensing device being operable to sense the uterine contractions of a pregnant woman and fetal heart rate,
wherein the signals are analysed with respect to any one or more of the following properties baseline heart rate, heart rate variability, heart rate acceleration, heart rate deceleration, uterine contraction frequency, uterine pushing classification, sinusoid classification, bimodal classification and sensing device output signal quality.

18. A method of analyzing and classifying an ongoing signal, the method comprising the steps of:
receiving a signal for analysis;
processing the received signal and identifying the occurrence of any of a plurality of predetermined signal features,
automatically incrementing or decrementing one or more distinct belief index values in response to the identification of predetermined signal features, wherein each distinct belief index corresponding to one of a plurality of potential signal classifications and further wherein said belief index values are used to calculate belief index ratings, wherein said belief index values are incremented or decremented according to an algorithm or a look up table of increments and/or decrements corresponding to the feature or features identified in the signal; and
obtaining an indication as to the overall signal classification by considering the relative belief index rating of each potential signal classification; and
displaying to an operator of said signal analyzer an indication of the classification of the signal based on the individual belief index values.

\* \* \* \* \*